United States Patent
Myers et al.

(10) Patent No.: US 9,095,577 B2
(45) Date of Patent: Aug. 4, 2015

(54) STABILIZED AMINE-CONTAINING ACTIVES IN ORAL FILM COMPOSITIONS

(71) Applicant: MonoSol Rx, LLC, Warren, NJ (US)

(72) Inventors: Garry L. Myers, Kingsport, TN (US); Madhu Sudan Hariharan, Munster, IN (US); Kevin Davidson, Valparaiso, IN (US); Pradeep Sanghvi, Dyer, IN (US)

(73) Assignee: MONOSOL RX, LLC, Warren, NJ (US)

( * ) Notice: Subject to any disclaimer, the term of this patent is extended or adjusted under 35 U.S.C. 154(b) by 0 days.

(21) Appl. No.: 14/635,851

(22) Filed: Mar. 2, 2015

(65) Prior Publication Data

US 2015/0174106 A1    Jun. 25, 2015

Related U.S. Application Data

(63) Continuation of application No. 12/835,394, filed on Jul. 13, 2010.

(60) Provisional application No. 61/224,962, filed on Jul. 13, 2009.

(51) Int. Cl.
| | |
|---|---|
| *A61K 47/00* | (2006.01) |
| *A61K 31/4178* | (2006.01) |
| *A61K 9/00* | (2006.01) |
| *A61K 47/10* | (2006.01) |
| *A61K 47/38* | (2006.01) |
| *A61K 47/02* | (2006.01) |
| *A61K 47/26* | (2006.01) |

(52) U.S. Cl.
CPC ............. *A61K 31/4178* (2013.01); *A61K 9/006* (2013.01); *A61K 47/02* (2013.01); *A61K 47/10* (2013.01); *A61K 47/26* (2013.01); *A61K 47/38* (2013.01)

(58) Field of Classification Search
CPC ................................................... A61K 9/0056
See application file for complete search history.

(56) References Cited

U.S. PATENT DOCUMENTS

| 2005/0075432 | A1* | 4/2005 | Verrall et al. ................ 524/284 |
| 2008/0075825 | A1* | 3/2008 | Fuisz et al. .................... 426/534 |
| 2008/0233174 | A1* | 9/2008 | Myers et al. .................. 424/435 |
| 2009/0004254 | A1* | 1/2009 | Maibach ....................... 424/444 |
| 2010/0297232 | A1* | 11/2010 | Myers et al. ................... 424/484 |

* cited by examiner

*Primary Examiner* — David J Blanchard
*Assistant Examiner* — Sarah Alawadi
(74) *Attorney, Agent, or Firm* — Hoffmann & Baron, LLP

(57) ABSTRACT

The present invention relates to compositions relating to films containing active pharmaceutical agents. In particular, the present invention relates to methods and systems useful for stabilizing amine-containing actives for dispersion in a film product.

16 Claims, No Drawings

STABILIZED AMINE-CONTAINING ACTIVES IN ORAL FILM COMPOSITIONS

CROSS-REFERENCE TO RELATED APPLICATIONS

This application is a continuation of U.S. patent Ser. No. 12/835,394, filed Jul. 13, 2010, which claims priority to U.S. Provisional Application No. 61/224,962, filed Jul. 13, 2009, the entire contents of which are incorporated by reference herein.

FIELD OF THE INVENTION

The present invention relates to compositions relating to films containing pharmaceutical agents, including biologicals, biopharmaceuticals, bioeffecting agents and prophylactic or therapeutic actives. In particular, the present invention relates to methods and systems useful for stabilizing amine-containing actives for incorporation in a film product.

BACKGROUND OF THE RELATED TECHNOLOGY

Providing administration of an active agent, such as a pharmaceutical active, in an oral film form is known to have substantial benefits over other dosage forms, such as tablets and the like. Generally, such oral films include a mixture of a polymer, solvent, the active, and flavorants, such as sweeteners and other flavor-enhancing components. A wet matrix of the components is prepared and then dried into a film dosage form.

In preparing such film dosage forms, uniformity of content of the film-forming matrix is important, so as to provide an even level of the active in individual film dosages. To achieve a uniform and even dispersion of components, it may be desired use a multi-step mixing process, where certain components are first mixed together, and then added to a third component. When various components are added to a polymer solution, it is beneficial that the components not form a gelatinous or plastic-like mass prior to addition to the polymer solution. As is readily understood by one of skill in the art, when the various components have such gelatinous composition, uniform and even dispersion throughout the polymeric matrix is difficult, if not impossible. It has been surprisingly discovered that the combination of certain actives and sweeteners has a tendency to result in an undesirable gel-like mass, which may be difficult to uniformly distribute throughout a polymeric matrix. Furthermore, it is difficult or impossible to spread a gel-like mass on to a substrate to produce a wet film for subsequent drying to form the dried film.

The present invention seeks to provide a method and system for preparing film dosages that overcomes the disadvantages in the prior art.

SUMMARY OF THE INVENTION

In one embodiment of the present invention, there is provided a method of preparing an edible film dosage composition, comprising the steps of: preparing a wet film matrix, said wet film matrix comprising a mixture of: a therapeutically effective amount of an active, said active comprising at least one free amine group; an electrolyte; a sweetener; at least one polymer; and drying said wet matrix to form an edible film dosage composition from said wet film matrix.

In another embodiment, there is provided a method of preparing an edible film dosage composition, comprising the steps of: preparing a slurry; said slurry comprising a mixture of: a therapeutically effective amount of an active, said active comprising at least one free amine group; an electrolyte; a sweetener; and a solvent; and preparing a polymeric matrix comprising at least one polymer; combining said slurry and polymeric matrix to form a wet matrix; and drying said wet matrix to form an edible film dosage composition from said wet film matrix.

The present invention further provides an edible film composition, comprising: a therapeutically effective amount of an active, said active comprising at least one free amine group; an electrolyte; a sweetener; and at least one polymer.

DETAILED DESCRIPTION OF THE PREFERRED EMBODIMENTS

The present invention provides a pharmaceutical composition in the form of a film for oral administration, including a composition having a uniformly distributed combination of a polymer, a polar solvent, a sweetening agent, and a pharmaceutically active or bioeffecting agent. The composition in its dried film form maintains a uniform distribution of components through the application of controlled bottom drying of the film.

It will be understood that the term "film" includes films, sheets and wafers, in any size and shape, including rectangular, square, or other desired shape. The films described herein may be any desired thickness and size such that it may be placed into the oral cavity of the user. For example, the films may have a relatively thin thickness of from about 0.1 to about 10 mils, or they may have a somewhat thicker thickness of from about 10 to about 30 mils. For some films, the thickness may be even larger, i.e., greater than about 30 mils. Films may be in a single layer or they may be multi-layered, such as laminated or co-extruded films.

Many additives used in making film compositions, such as sweeteners, flavors, and various excipients, include chemical groups which may undesirably interact with actives during or after processing. For example, it has been discovered that interactions between sweeteners containing available halogen groups may interact with actives containing available amine groups to cause gellation or agglomeration. Such undesirable interaction interferes with the ability to properly process matrices for forming uniform and acceptable dosage forms. The films and processes described herein may include the combination of two components which may undesirably react during or after processing. For example, one component may have a reactive group, such as a halogen, amine, acid, and a second component may have another free group which may be likely to react with the free group of the first component. In one particular process, a first component includes a nucleophilic heterocyclic active, which reacts with an alkyl halide to form a quaternary salt. The processes described herein may be useful in preventing or at least reducing the likelihood of undesirable reaction of these groups.

The film dosage composition preferably includes a polymeric carrier matrix, also referred to as a wet film-forming matrix. Any desired polymeric carrier matrix may be used, provided that it is orally dissolvable and is suitable for human ingestion. The orally consumable films are preferably fast-dissolving or moderate-dissolving in the oral cavity and particularly suitable for delivery of actives. However, controlled and sustained release compositions are also among the various embodiments contemplated by the present invention.

The films used in the pharmaceutical products may be produced by a combination of at least one polymer and a polar solvent, optionally including other fillers known in the art. The solvent may be water, a polar organic solvent including, but not limited to, ethanol, isopropanol, acetone, or any combination thereof. The film may be prepared by utilizing a selected casting or deposition method and a controlled drying process. For example, the film may be prepared through controlled drying processes, which include application of heat and/or radiation energy to the wet film matrix to form a visco-elastic structure in a short period of time (such as less than 10 minutes), thereby controlling the uniformity of content of the film. Such processes are described in more detail in commonly assigned U.S. Pat. Nos. 7,425,292 and 7,357,891, the contents of which are incorporated herein by reference in their entirety. Alternatively, the films may be extruded as described in commonly assigned U.S. application Ser. No. 10/856,176, filed on May 28, 2004, and published as U.S. Patent Publication No. 2005/0037055 A1, the contents of which are incorporated herein by reference in their entirety.

The polymer(s) included in the films may be water-soluble, water-swellable, water-insoluble, or a combination of one or more either water-soluble, water-swellable or water-insoluble polymers. As used herein the phrase "water-soluble polymer" and variants thereof refer to a polymer that is at least partially soluble in water, and desirably fully or predominantly soluble in water, or absorbs water. Polymers that absorb water are often referred to as being water-swellable polymers. The materials useful with the present invention may be water-soluble or water-swellable at room temperature and other temperatures, such as temperatures exceeding room temperature. Moreover, the materials may be water-soluble or water-swellable at pressures less than atmospheric pressure. Desirably, the water-soluble polymers are water-soluble or water-swellable having at least 20 percent by weight water uptake. Water-swellable polymers having a 25 or greater percent by weight water uptake are also useful. In some embodiments, films formed from such water-soluble polymers may be sufficiently water-soluble to be dissolvable upon contact with bodily fluids. The polymer may include cellulose or a cellulose derivative.

Specific examples of useful polymers include, but are not limited to, polyethylene oxide, pullulan, hydroxypropylmethyl cellulose, hydroxyethyl cellulose, hydroxypropyl cellulose, polyvinyl pyrrolidone, carboxymethyl cellulose, polydextrose, polyvinyl alcohol, sodium alginate, propylene glycol alginate, carrageenan, polyethylene glycol, xanthan gum, tragancanth gum, guar gum, acacia gum, arabic gum, polyacrylic acid, methylmethacrylate copolymer, copolymers of acrylic acid and alkyl acrylate (available as Pemulen® polymers), carboxyvinyl copolymers, starch, gelatin, pectin, and combinations thereof. Specific examples of useful water-insoluble polymers include, but are not limited to, ethyl cellulose, hydroxypropyl ethyl cellulose, cellulose acetate phthalate, hydroxypropyl methyl cellulose phthalate and combinations thereof.

Other polymers useful for incorporation into the films include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Specific examples of useful water insoluble polymers include, but are not limited to, ethyl cellulose, hydroxypropyl ethyl cellulose, cellulose acetate phthalate, hydroxypropyl methyl cellulose phthalate, acrylic polymers, vinyl acetate, sodium sulphonated polyesters, carboxylated acrylics, trimethylpentanediol/adipic acid/glycerin cross polymer, polyglycerol-2-diisostearate/IPDI copolymer, carboxylated vinyl acetate copolymer, vinylpyrrolicone/vinyl acetate/alkylaminoacrylate terpolymers, vinylpyrrolidone/vinyl acetate copolymer, and combinations thereof.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.). The Biodel materials represent a family of various polyanhydrides which differ chemically.

Although a variety of different polymers may be used, it is desired to select polymers that provide mucoadhesive properties to the film, as well as a desired dissolution and/or disintegration rate. In particular, the time period for which it is desired to maintain the film in contact with the mucosal tissue depends on the type of active contained in the second delivery vehicle. Some actives may only require a few minutes for delivery through the mucosal tissue, whereas other actives may require up to several hours or even longer. Accordingly, in some embodiments, one or more water-soluble polymers, as described above, may be used to form the film. In other embodiments, however, it may be desirable to use combinations of water-soluble polymers and polymers that are water-swellable, water-insoluble and/or biodegradable, as provided above. The inclusion of one or more polymers that are water-swellable, water-insoluble and/or biodegradable may provide films with slower dissolution or disintegration rates than films formed from water-soluble polymers alone. As such, the film may adhere to the mucosal tissue for longer periods or time, such as up to several hours, which may be desirable for delivery of certain active ingredients.

Oral dissolving films generally fall into three main classes: fast dissolving, moderate dissolving and slow dissolving. Fast dissolving films generally dissolve in about 1 second to about 30 seconds. Moderate dissolving films generally dissolve in about 1 to about 30 minutes, and slow dissolving films generally dissolve in more than 30 minutes, e.g., up to about 60 minutes or more. Fast dissolving films may consist of low molecular weight hydrophilic polymers (i.e., polymers having a molecular weight between about 1,000 to 200,000). In contrast, slow dissolving films generally have high molecular weight polymers (i.e., having a molecular weight in the millions).

Moderate dissolving films tend to fall in between the fast and slow dissolving films. Moderate dissolving films dissolve rather quickly, but also have a good level of mucoadhesion. Moderate films are also flexible, quickly wettable, and are typically non-irritating to the user. For the instant invention, it is preferable to use films that are either fast-dissolving or that fall between the categories of fast dissolving and moderate dissolving. Such films provide a quick enough dissolution rate (between about 1 minute and about 5 minutes), while providing an acceptable mucoadhesion level such that the film is not easily removable once it is placed in the oral cavity of the user.

Desirably, the individual film dosage has a small size that is between about 0.5-1 inch by about 0.5-1 inch. Most preferably, the film dosage is about 0.75 inches×0.5 inches. The film dosage should have good adhesion when placed in the oral cavity of the user. Further, the film dosage should disperse and dissolve at a moderate rate, that is, between about 1 minute to about 60 minutes, and more desirably between about 5 minutes and about 30 minutes, and more desirably about 10 minutes to about 60 minutes. In some embodiments, however, it is particularly desirable to allow the individual film dosage to dissolve slowly, over a period of longer than about 30 minutes.

The films of the present invention may include more than one polymer. For instance, in some embodiments, the films may include polyethylene oxide alone or in combination with a second polymer component. In some embodiments, the films may include polymers other than polyethylene oxide. The second polymer may be another water-soluble polymer, a water-swellable polymer, a water-insoluble polymer, a biodegradable polymer or any combination thereof. Suitable water-soluble polymers include, without limitation, any of those provided above.

In accordance with some embodiments, polyethylene oxide may range from about 10% to 100% by weight in the polymer component, more specifically about 20% to about 70% by weight, and even more specifically about 20% to about 60% by weight. In some embodiments, one or more water-swellable, water-insoluble and/or biodegradable polymers also may be included in the polyethylene oxide-based film. Any of the water-swellable, water-insoluble or biodegradable polymers provided above may be employed. The second polymer component, which may be, for example, a cellulosic polymer, may be employed in amounts of about 0% to about 80% by weight in the polymer component, more specifically about 20% to about 70% by weight, and even more specifically about 20% to about 60% by weight.

The molecular weight of the polyethylene oxide also may be varied. In some embodiments, high molecular weight polyethylene oxide, such as about 4 million, may be desired to increase mucoadhesivity of the film. In some other embodiments, the molecular weight may range from about 100,000 to 900,000, more specifically from about 100,000 to 600,000, and even more specifically from about 100,000 to 300,000. In some embodiments, it may be desirable to combine high molecular weight (600,000 to 900,000) with low molecular weight (100,000 to 300,000) polyethylene oxide in the polymer component.

A variety of optional components and fillers also may be added to the films. These may include, without limitation: surfactants; plasticizers; polyalcohols; anti-foaming agents, such as silicone-containing compounds, which promote a smoother film surface by releasing oxygen from the film; thermo-setting gels such as pectin, carageenan, and gelatin, which help in maintaining the dispersion of components; inclusion compounds, such as cyclodextrins and caged molecules; coloring agents; and flavors. In some embodiments, more than one active ingredient may be included in the film.

Additives may be included in the films. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active agent(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water-soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all film components.

Further additives may be inorganic fillers, glidants and opacifiers, such as the oxides of magnesium aluminum, silicon, titanium, etc. desirably in a concentration range of about 0.02% to about 3% by weight and desirably about 0.02% to about 1% based on the weight of all film components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins may be up to about 5% and preferably within the range of about 0.5% to about 2% by weight of the total film composition.

It further may be useful to add silicon dioxide, calcium silicate, or titanium dioxide in a concentration of about 0.02% to about 1% by weight of the total composition. These compounds act as flow agents.

Lecithin is one surface active agent for use in the films described herein. Lecithin may be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB").

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols. If desired, the film may include other additives, such as keratin, or proteins, including proteins that are useful in forming a gel, such as gelatine.

Further potential additives include solubility enhancing agents, such as substances that form inclusion compounds with active ingredients. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Suitable coloring agents include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

The films may include one or more additives to provide a taste masking of the active ingredient. For example, the films may include ionic exchange resins, including but not limited to a water-insoluble organic or inorganic matrix material having covalently bound functional groups that are ionic or capable of being ionized under appropriate conditions. The organic matrix may be synthetic (e.g., polymers or copolymers or acrylic acid, methacrylic acid, sulfonated styrene or sulfonated divinylbenzene) or partially synthetic (e.g., modified cellulose or dextrans). The inorganic matrix may be, for example, silica gel modified by the addition of ionic groups. Most ion exchange resins are cross-linked by a crosslinking agent, such as divinylbenzene.

Anti-foaming and/or de-foaming components may also be used with the films. These components aid in the removal of air, such as entrapped air, from the film-forming compositions. Such entrapped air may lead to non-uniform films. Simethicone is one particularly useful anti-foaming and/or de-foaming agent. The present invention, however, is not so limited and other anti-foam and/or de-foaming agents may be used.

As a related matter, simethicone and related agents may be employed for densification purposes. More specifically, such agents may facilitate the removal of voids, air, moisture, and similar undesired components, thereby providing denser, and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films, the mixing step may be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles during and after mixing.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Any other optional components described in commonly assigned U.S. Pat. Nos. 7,425,292 and 7,357,891 and U.S. application Ser. No. 10/856,176, referred to above, also may be included in the films described herein.

Various active ingredients may be included in the film, including pharmaceutical actives or bioeffecting agents. Preferably, the active ingredients may be dispersed throughout the polymeric matrix uniformly so as to provide a controlled and equally dispersed dosage form.

In one particular embodiment, the active ingredient includes at least one amine-containing active, such as ondansetron. The active ingredient may include the amine-containing active by itself or in combination with other active ingredients. The amine group may be primary, secondary or tertiary amine. As set forth above, the amine-containing active is desirably dispersed throughout the film-forming matrix uniformly, so as to provide an adequate dosage of the amine-containing active in the resultant film product.

As explained above, ondansetron is one particular amine-containing active. The structure of ondansetron is set forth below:

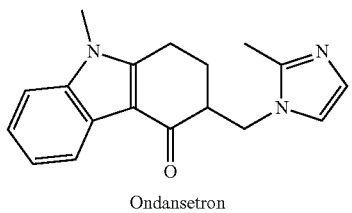 [SMILES: Cc1nccn1CC1CCc2c(c3ccccc3n2C)C1=O]

Ondansetron

In an oral film dosage, it is particularly useful to include at least one flavor-enhancing component so as to provide a suitable taste to the user. In some embodiments, the film products include a sweetener. In some methods of manufacture, it is useful to combine the active with sweeteners and other flavor-enhancing components to form a slurry, and then disperse the slurry throughout a polymeric matrix. Such multi-step mixing procedure may aid in even and uniform dispersion of the active. It has been found, however, that the combination of certain amine-containing actives and certain additives, particularly those which have primary alkyl halides, may result in the formation of an gel-like mass. One such additive is sucralose, a sweetener that contains a primary alkyl chloride. When this gel-like mass is added to the polymer solution, even and uniform dispersion of the active is difficult, if not impossible, to achieve. Furthermore, the resulting dispersion cannot be spread as a film due to the presence of non-homogeneous clumps within the dispersion.

The present invention provides a method of preparing a film product incorporating an amine-containing active and a sweetener, the sweetener having at least one primary alkyl halide group. Sucralose, for example, is a sweetener that has primary alkyl chlorides available. When sucralose is combined with an amine-containing active, the primary alkyl chlorides may interact with the amines on the amine-containing active pharmaceutical ingredient to form quaternary salts or may otherwise affect the zeta potential at the surface of the drug particles. The quaternary salt compounds may form ionic associations amongst themselves to immobilize the surrounding media (water) in which it is suspended to produce hydrogel like structures resulting in what may appear like a flocculated mass in suspension. Such interactions result in an undesirable gel-like mass/flocculate which depending on the concentration of the charged species in solution may eventually result in a unstable flocculate that may settle in solution and form a hard cake. This deflocculated cake at the bottom of the suspension may be difficult or impossible to re-disperse. By using the methods set forth herein, the formation of a gel-like mass can be avoided, and a suitable, uniform film product can be obtained. Desirably, films of the present invention are prepared using a multi-step mixing procedure, whereby the process of forming the wet film-forming matrix is performed via multiple steps. This process is contrary to other "one step mixing procedures", where one portion of the solvent is used to mix the active ingredient and all excipients together. A one step mixing procedure may undesirably form an agglomeration of components, making a uniform mixture difficult to achieve.

In one particular multi-step mixing procedure, a dispersion is first prepared including the amine-containing active pharmaceutical ingredient and various additives, solvents, and/or excipients. The active slurry may include any desired components, including sweeteners, flavors, colorants, chelating agents, and other excipients. The slurry may further include one or more solvents, including polar solvents such as water. The solvent may be present in any desired amount, such as between about 50-80% by weight of the slurry, and most desirably about 60% by weight of the slurry. The active-containing slurry may then be then added to a separate polymer solution to form a wet film-forming matrix. The polymer solution preferably contains the polymer or polymers to be used in the film, along with additional solvents and other desired components. It is desirable to form the amine-containing active slurry prior to adding to the polymer solution so as to adequately disperse the active ingredient in the polymer solution by breaking or removing most if not all of the amine-containing active pharmaceutical ingredient agglomerates that may have formed.

Since the polymer solution is relatively viscous, the formation of a solvent-based slurry, which is less viscous than the polymer solution, allows higher shear. A higher shear results in a wet film-forming matrix that can readily reduce the amount of agglomerates in the matrix. It is thus desired to use a slurry that is relatively free of agglomeration, and has a relatively low viscosity. In one embodiment, the method of forming the film product includes forming a slurry by first combining the amine-containing active pharmaceutical ingredient and a suitable electrolyte (e.g. a weak base salt of an acid such as monoammonium glycyrrhizinate—including that sold under the trade name Magnasweet®, manufactured by Mafco Worldwide Corporation). Other electrolytes may also be used. The advantage of Magnasweet is that it also serves as a secondary flavor enhancer/sweetener.

As explained above, the combination of an amine-containing active ingredient with a component that includes primary alkyl halide groups may form undesirable agglomerates that result in immobilization of the dispersion medium by formation of a hydrogel. The present invention provides a means to counteract this effect. It was found that the addition of a suitable electrolyte to the amine-containing active ingredient modifies the surface charges on the suspended API particles and prevents the strong electrophilic interaction of the alkyl chloride and the amines available on the amine-containing active component, e.g., a pharmaceutical or bioeffecting component. As such, there is no gel-like mass formation or agglomeration of components. For example, in a combination of ondansetron with monoammonium glycyrrhizinate, the amines of the ondansetron form an equilibrium with the ammonium ions of the monoammonium glycyrrhizinate. The combination of ondansetron and monoammonium glycyrrhizinate may then be combined with sucralose, for example, without concern as to the formation of a gel like mass. The resulting combination may then be mixed with a polymeric solution to form the wet film-forming matrix. The wet matrix may then be cast and dried to form the film dosage.

The order of mixing of the various components may be varied. In some embodiments, the active component, e.g., a pharmaceutical or bioaffecting active, and the electrolyte may first be combined, and then added to the primary alkyl chloride-containing component. In other embodiments, the active, the electrolyte, and the sweetener may be combined at or about the same time. Once the components have been combined to form the active-containing slurry, the active-containing slurry may be dispensed throughout a polymer mixture to form the wet film-forming matrix. Once the components have all been combined, the wet film-forming matrix may be cast and dried to form the film product.

In some embodiments, the dosage form may include the salt form of the active ingredient, such as, for example, ondansetron HCl. In such embodiments, the salt form of the active ingredient may not react unfavorably with the primary alkyl halide-containing additive, and thus there may be no need to combine the active with an electrolyte. In this embodiment, the salt form of the active may form a slurry with sweeteners and other excipients, either with or without inclusion of an electrolyte. The resulting slurry may then be dispersed throughout the polymeric solution to form the wet film-forming matrix.

It has been discovered that gellation and/or agglomeration of components particularly occurred when sucralose was added to the active ingredient (such as ondansetron). It has been determined that the particular choice of excipients combined together may be important to prevent the formation of undesirable gellation and/or agglomeration. As will be described in more detail in the Example below, inclusion of an electrolyte was shown to prevent the gellation. In particular, inclusion of monoammonium glycyrrhizinate was found to prevent gellation. Water concentration, pH, and the use of a chelating agent did not appear to have an impact on the formation or prevention of the gellation. It is hypothesized that the amines on the active component may form quaternary salts with the primary alkyl chlorides on the sucralose. Quaternary polymers make good hydrogels, and thus undesirably form a gel-like structure, which is problematic in the processing of film matrices to form films having a uniformity of content. The Applicants further noted that sucrose did not react with the amine-containing active, which demonstrates that the normal carbohydrate functionality is not the cause of the gel formation.

The presently described technology and its advantages will be better understood by reference to the following Examples. These examples are provided to describe specific embodiments of the present technology. By providing these specific examples, the applicants do not limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Laboratory Scale Batches

A one step mixing procedure was used to prepare an active film including a polymeric matrix and ondansetron, along with sweeteners and excipients, including sucralose. The one step mix procedure formed an active film that had agglomerates, and therefore failed to provide a uniformly dispersed film product. Various mix procedures were tried to determine if there was a procedure that would eliminate the cause of the agglomerates. The various mix procedures tried during this time did show that the agglomerates could be reduced/eliminated using a "multi step mix procedure".

Three distinct solution(s)/suspension(s) were made separately then combined to form the final coating suspension. The three solution(s)/suspension(s) included the following: active pharmaceutical ingredient (API) in aqueous suspension, flavor solution and aqueous polymer solution. Water was the primary solvent for the final coating suspension. The water was divided into three portions, one portion of water was used to mix the API and other select ingredients forming an API suspension (or slurry), a second portion of water was used to mix the polymers, and the final portion of water was used for rinsing of the container which contained the API slurry. A flavor solution was made by adding butylated hydroxytoluene (antioxidant) to a peppermint flavor.

During the re-evaluation phase of the mix procedure, various compositions of the API slurry were examined. Initially, ondansetron, BHT, xanthan gum, erythritol, fumed silica, monoammonium glycyrrhizinate, sodium bicarbonate, titanium dioxide, sucralose and precipitated calcium carbonate were all added directly to the portion of water used for the API suspension. This API suspension was then added to the polymer solution and the resulting active film was free from fine agglomerates. The portion of water set aside for the API suspension during these batches ranged from 20-30% of the total available water for the formulation while the portion of water set aside for the polymer solution was consistently 70%.

Pilot Scale Batches in Commercial Manufacturing Equipment

From the results of Example 1 above, it appeared that the multi-step mixing procedure used in the laboratory and described above provided a film product that was free of agglomerates. The process was then transferred to the commercial scale equipment. During this transition, the composition of the API slurry of example 1 was changed to allow for a more robust mixing process. The new composition of the API slurry consisted of the API, the non water soluble excipients (precipitated calcium carbonate and titanium dioxide), sucralose and fumed silica (Cab-O-Sil M5P).

It was determined that the amount of water used for the polymer portion could be reduced, and therefore there would be more flexibility in allocating more water for the API suspension as well as potentially increasing the amount of rinse water. This batch also highlighted a potential processing issue regarding the addition of sucralose. To prevent the drop tube from plugging during Sucralose addition, the decision was made to add the sucralose to the API suspension for future batches. At this time, the addition of the Sucralose to the API suspension was deemed acceptable, as they had been included together in the API suspension made previously on the lab scale.

The water percentages used for the different steps for this batch are compared in Table 1 below.

TABLE 1

Water percentages for the pilot scale batch

|  | API Batch |
|---|---|
| Water for API suspension (%) | 20 |
| Water for Polymer Solution (%) | 70 |
| Water for rinsing (%) | 10 |

The mixing procedure was as follows. First, water was distributed in three portions as set forth in Table 1. Three solutions were separately prepared: the API suspension, the flavor solution, and the polymer solution. The API suspension used in this batch included the following: Ondansetron, precipitated calcium carbonate, Titanium Dioxide, Sucralose and fumed silica. These materials were mixed with the intention of producing a uniform flowable slurry. Simultaneously, the flavor solution was prepared by adding BHT to a peppermint flavor and mixed until dissolved. The polymer solution was likewise prepared, which included the steps of adding polyethylene oxide to the Water for Polymer Solution and mixing for 15 minutes. To this mixture, Methocel was added and mixed for 20 minutes.

During the step of adding the API suspension to the polymer solution, it was surprisingly noted that the API suspension had agglomerated to form a gel-like consistency. This phenomenon had not been observed in the preparation of the laboratory batch. n additional 5 kg of water was introduced in the API suspension mass. The addition of water did not break up the gel and the material still could not be mixed freely. However the additional water did allow the API gel like mass to be diluted and handled better so that it could be added to the polymer solution with a spatula into the top of the mix tank. The flavor solution was then added and the coating suspension was mixed and degassed under vacuum for 60 minutes. However, the final suspension still had agglomerates throughout the suspension that could not be redispersed.

Due to the unexpected outcome of the API suspension, it was determined that the mixing process could not be used successfully used as is at the manufacturing scale. Instead the mixing process was re-examined at the laboratory scale to determine the root cause of the formation of the hard gel like agglomerate and to establish a revised procedure for subsequent batches at the manufacturing scale.

Determination of Root Cause

In order to further investigate the reason for the observations in Example 2 above, a series of experiments were conducted. Two sets of experiments were initially conducted each of which was made at the 15 g scale.

In this set of experiments, the goal was to replicate the conditions during the processing of the pilot scale batch. This was achieved by using a series of samples, which included various percentages of components. Sample A consisted of the same formula of the API slurry that was performed in the pilot scale batch. Samples B-E were then prepared, which consisted of the API and one ingredient being added to water and mixed together to single out which ingredient was responsible for the reaction. Samples F and G were prepared, which were designed to determine which ingredient used in the original multi step process would prevent the formation of the agglomerate. The compositions of the Samples are shown in Table 2 below.

TABLE 2

| Compositions of Samples A-G | | | | | | | |
|---|---|---|---|---|---|---|---|
|  | Sample A | Sample B | Sample C | Sample D | Sample E | Sample F | Sample G |
| DI Water (%) | 65.09 | 72.57 | 73.62 | 79.80 | 79.80 | 64.33 | 64.71 |
| Ondansetron Base (%) | 15.31 | 17.08 | 17.32 | 18.78 | 18.78 | 15.14 | 15.22 |
| Precipitated calcium carbonate (%) | 9.28 | 10.35 | N/A | N/A | N/A | 9.17 | 9.23 |
| Sucralose (%) | 8.00 | N/A | 9.06 | N/A | N/A | 7.91 | 7.96 |
| Titanium Dioxide (%) | 1.16 | N/A | N/A | 1.42 | N/A | 1.15 | 1.15 |
| Fumed silica (%) | 1.16 | N/A | N/A | N/A | 1.42 | 1.15 | 1.15 |
| Sodium Bicarbonate (%) | N/A | N/A | N/A | N/A | N/A | 1.15 | N/A |

TABLE 2-continued

Compositions of Samples A-G

| | Sample A | Sample B | Sample C | Sample D | Sample E | Sample F | Sample G |
|---|---|---|---|---|---|---|---|
| Monoammonium glycyrrhizinate (%) | N/A | N/A | N/A | N/A | N/A | N/A | 0.087 |
| Total (%) | 100.00 | 100.00 | 100.00 | 100.00 | 100.00 | 100.00 | 100.00 |
| Did Gelling occur (Y/N) | Y | N | Y | N | N | Y | N |

As can be seen in Table 2, Sample C demonstrated that the composition including sucralose resulted in gellation when mixed with Ondansetron in water. Samples F and G were then prepared, which included sucralose in combination with sodium bicarbonate and monoammonium glycyrrhizinate, respectively. In Sample F, it was shown that the use of the sodium bicarbonate did not prevent the gellation/agglomeration. However, as demonstrated in Sample G, inclusion of monoammonium glycyrrhizinate was shown to prevent the gellation/agglomeration.

The invention claimed is:

1. An edible film dosage composition consisting of:
   a. ondansetron;
   b. a polymeric carrier matrix consisting of:
      i. hydroxypropylmethyl cellulose, and
      ii. polyethylene oxide;
   c. erythritol;
   d. peppermint flavor;
   e. calcium carbonate;
   f. sucralose;
   g. sodium bicarbonate;
   h. fumed silica;
   i. titanium dioxide;
   j. monoammonium glycyrrhizinate;
   k. xanthan gum; and
   l. butylated hydroxytoluene.

2. The edible film dosage composition of claim 1, wherein said polyethylene oxide is present in an amount of from about 20% to about 70% by weight and said hydroxypropylmethyl cellulose is present in an amount of from about 20% to about 70% by weight based on the total weight of the polymeric carrier matrix.

3. The edible film dosage composition of claim 1, wherein said polyethylene oxide is present in an amount of from about 20% to about 60% by weight and said hydroxypropylmethyl cellulose is present in an amount of from about 20% to about 60% by weight based on the total weight of the polymeric carrier matrix.

4. The edible film dosage composition of claim 1, wherein said titanium dioxide is present in an amount of from about 0.02 to about 3% by weight based on the total weight of the edible film dosage composition.

5. The edible film dosage composition of claim 1, wherein said titanium dioxide is present in an amount of from about 0.02 to about 1% by weight based on the total weight of the edible film dosage composition.

6. An edible film dosage composition consisting of:
   a. ondansetron;
   b. a polymeric carrier matrix consisting of:
      i. hydroxypropylmethyl cellulose;
   c. erythritol;
   d. peppermint flavor;
   e. calcium carbonate;
   f. sucralose;
   g. sodium bicarbonate;
   h. fumed silica;
   i. titanium dioxide;
   j. monoammonium glycyrrhizinate;
   k. xanthan gum; and
   l. butylated hydroxytoluene,
   wherein the amount of monoammonium glycyrrhizinate is sufficient to prevent the strong electrophilic interaction of the alkyl chloride groups of the sucralose with the amine groups of the ondansetron and thereby prevent the agglomeration of the ondansetron and sucralose.

7. The edible film dosage composition of claim 6, wherein said titanium dioxide is present in an amount of from about 0.02 to about 3% by weight based on the total weight of the edible film dosage composition.

8. The edible film dosage composition of claim 6, wherein said titanium dioxide is present in an amount of from about 0.02 to about 1% by weight based on the total weight of the edible film dosage composition.

9. An edible film dosage composition consisting of:
   a. ondansetron;
   b. a polymeric carrier matrix consisting of:
      i. hydroxypropylmethyl cellulose;
   c. erythritol;
   d. peppermint flavor;
   e. calcium carbonate;
   f. sucralose;
   g. sodium bicarbonate;
   h. fumed silica;
   i. titanium dioxide;
   j. monoammonium glycyrrhizinate;
   k. xanthan gum; and
   l. butylated hydroxytoluene,
   wherein the amounts of ondansetron and monoammonium glycyrrhizinate are sufficient for the amines groups of the ondansetron to form an equilibrium with the ammonium ions of the monoammonium glycyrrhizinate.

10. The edible film dosage composition of claim 8, wherein said titanium dioxide is present in an amount of from about 0.02 to about 3% by weight based on the total weight of the edible film dosage composition.

11. The edible film dosage composition of claim 8, wherein said titanium dioxide is present in an amount of from about 0.02 to about 1% by weight based on the total weight of the edible film dosage composition.

12. An edible film dosage composition consisting of:
   a. ondansetron;
   b. a polymeric carrier matrix consisting of:
      i. hydroxypropylmethyl cellulose, and
      ii. polyethylene oxide;
   c. erythritol;
   d. peppermint flavor;
   e. calcium carbonate;
   f. sucralose;
   g. sodium bicarbonate;
   h. fumed silica;

i. titanium dioxide;
j. monoammonium glycyrrhizinate;
k. xanthan gum; and
l. butylated hydroxytoluene, wherein the amount of monoammonium glycyrrhizinate is sufficient to prevent the strong electrophilic interaction of the alkyl chloride groups of the sucralose with the amine groups of the ondansetron and thereby prevent the agglomeration of the ondansetron and sucralose, and/or wherein the amounts of ondansetron and monoammonium glycyrrhizinate are sufficient for the amines groups of the ondansetron to form an equilibrium with the ammonium ions of the monoammonium glycyrrhizinate.

13. The edible film dosage composition of claim 12, wherein said polyethylene oxide is present in an amount of from about 20% to about 70% by weight and said hydroxypropylmethyl cellulose is present in an amount of from about 20% to about 70% by weight based on the total weight of the polymeric carrier matrix.

14. The edible film dosage composition of claim 12, wherein said polyethylene oxide is present in an amount of from about 20% to about 60% by weight and said hydroxypropylmethyl cellulose is present in an amount of from about 20% to about 60% by weight based on the total weight of the polymeric carrier matrix.

15. The edible film dosage composition of claim 12, wherein said titanium dioxide is present in an amount of from about 0.02 to about 3% by weight based on the total weight of the edible film dosage composition.

16. The edible film dosage composition of claim 12, wherein said titanium dioxide is present in an amount of from about 0.02 to about 1% by weight based on the total weight of the edible film dosage composition.

* * * * *